US008648265B2

(12) United States Patent
Talamine et al.

(10) Patent No.: US 8,648,265 B2
(45) Date of Patent: Feb. 11, 2014

(54) FULL PERIMETER LASER BEAM BUTTON WELD OF DISSIMILAR MATERIALS

(75) Inventors: Ken Talamine, Amherst, NY (US); Keith Seitz, Clarence Center, NY (US); Tim Weiskopff, Amherst, NY (US); Donald Anthony Bonitati, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 253 days.

(21) Appl. No.: 13/155,497

(22) Filed: Jun. 8, 2011

(65) Prior Publication Data

US 2011/0297439 A1  Dec. 8, 2011

Related U.S. Application Data

(60) Provisional application No. 61/352,612, filed on Jun. 8, 2010.

(51) Int. Cl.
*H02G 3/18* (2006.01)

(52) U.S. Cl.
USPC .............. 174/520; 174/650; 607/37; 361/302

(58) Field of Classification Search
USPC .......... 174/650, 50.6, 35 R; 361/302; 607/37; 29/876
See application file for complete search history.

(56) References Cited

U.S. PATENT DOCUMENTS

| 4,252,263 | A | 2/1981 | Houston |
|---|---|---|---|
| 4,678,868 | A | 7/1987 | Kraska |
| 5,250,373 | A | 10/1993 | Muffoletto et al. |
| 5,571,146 | A | 11/1996 | Jones et al. |
| 5,750,286 | A | 5/1998 | Paulot et al. |
| 5,877,472 | A | 3/1999 | Campbell et al. |
| 6,061,595 | A | 5/2000 | Safarevich |
| 6,131,796 | A | 10/2000 | Kaja et al. |
| 6,221,513 | B1 | 4/2001 | Lasater |
| 6,503,640 | B2 | 1/2003 | Wittebrood et al. |
| 6,852,925 | B2 * | 2/2005 | Wolf et al. .................... 174/50.6 |
| 6,929,881 | B2 | 8/2005 | Wutz et al. |
| 6,932,879 | B2 | 8/2005 | Ely et al. |
| 7,145,076 | B2 * | 12/2006 | Knappen et al. ............. 174/50.6 |
| 7,186,049 | B1 | 3/2007 | Grubb et al. |
| 7,341,802 | B1 | 3/2008 | Ota et al. |
| 7,539,007 | B2 | 5/2009 | Zhao et al. |
| 7,544,220 | B2 | 6/2009 | Zhao et al. |
| 7,564,674 | B2 * | 7/2009 | Frysz et al. .................... 361/302 |
| 7,622,219 | B2 | 11/2009 | Ota et al. |
| 2004/0038070 | A1 | 2/2004 | Dockus et al. |
| 2005/0007718 | A1 | 1/2005 | Stevenson |
| 2006/0174463 | A1 | 8/2006 | O'Phelan |
| 2008/0171952 | A1 | 7/2008 | Mishima |

OTHER PUBLICATIONS

European Search Report dated Sep. 30, 2011.

* cited by examiner

*Primary Examiner* — Dhirubhai R Patel
(74) *Attorney, Agent, or Firm* — Michael F. Scalise

(57) ABSTRACT

Terminal pins that include a refractory metal forming a full perimeter weld connected to a terminal block including a dissimilar metal incorporated into feedthrough filter capacitor assemblies are discussed. The feedthrough filter capacitor assemblies are particularly useful for incorporation into implantable medical devices such as cardiac pacemakers, cardioverter defibrillators, and the like, to decouple and shield internal electronic components of the medical device from undesirable electromagnetic interference (EMI) signals.

26 Claims, 9 Drawing Sheets

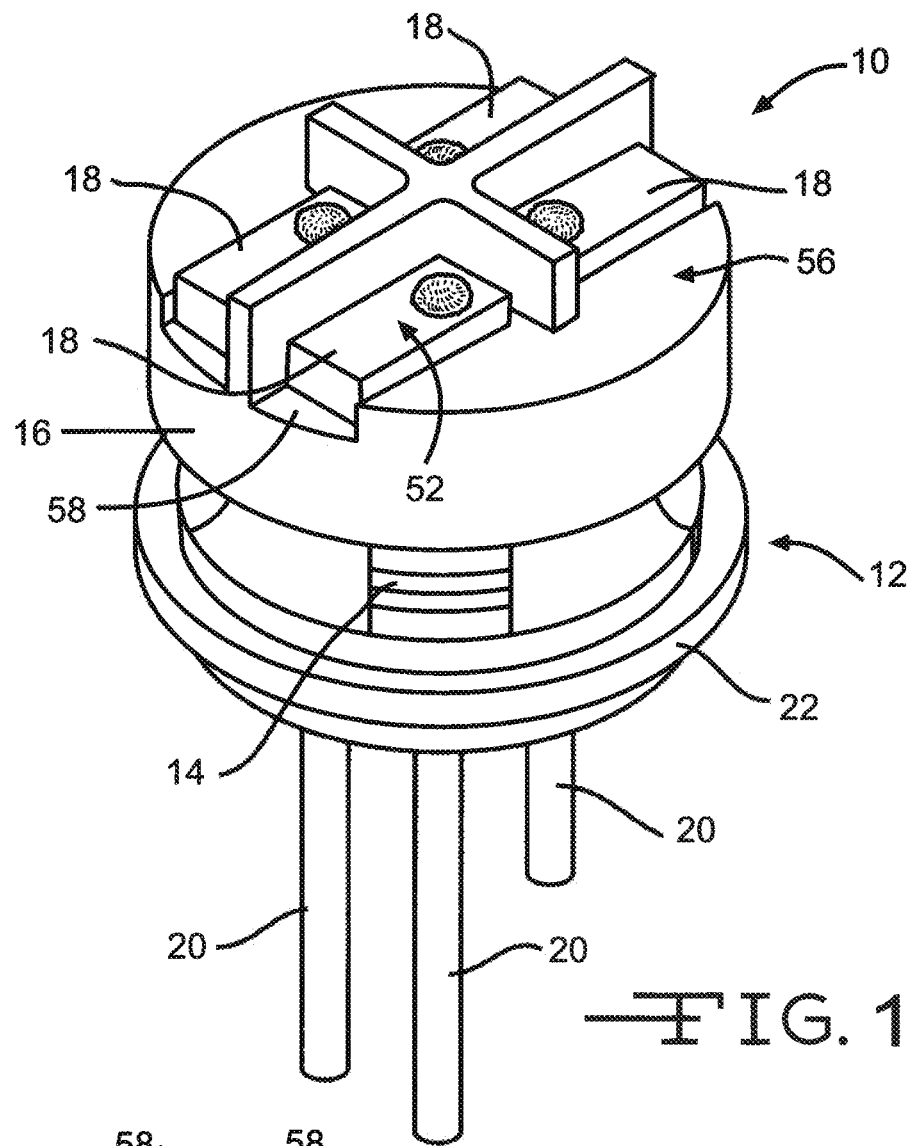
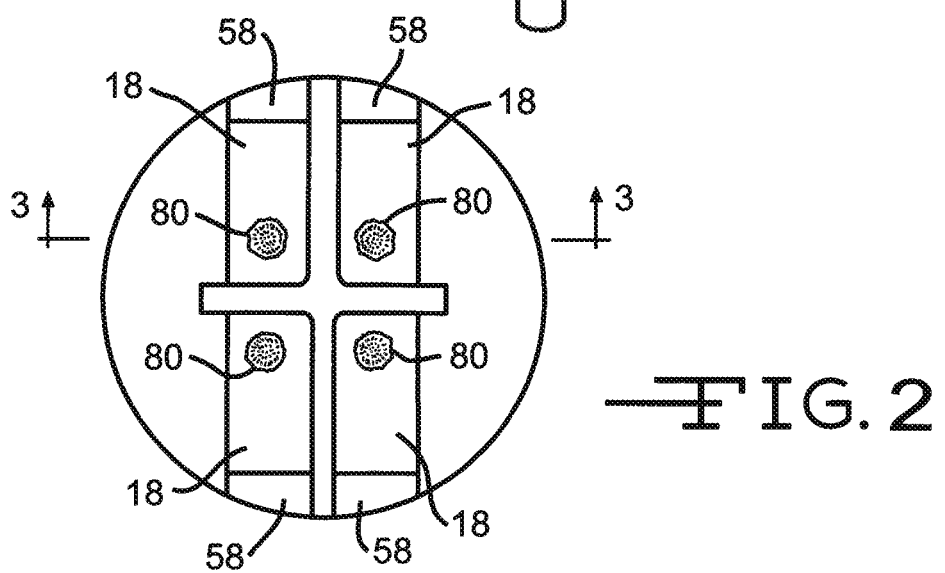

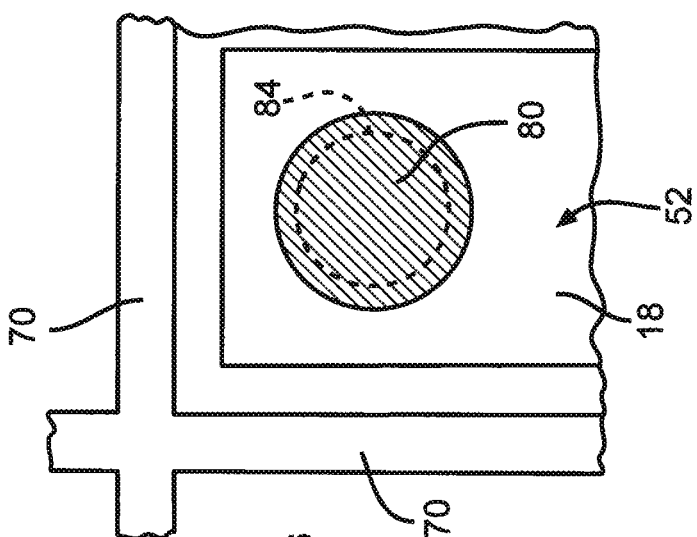
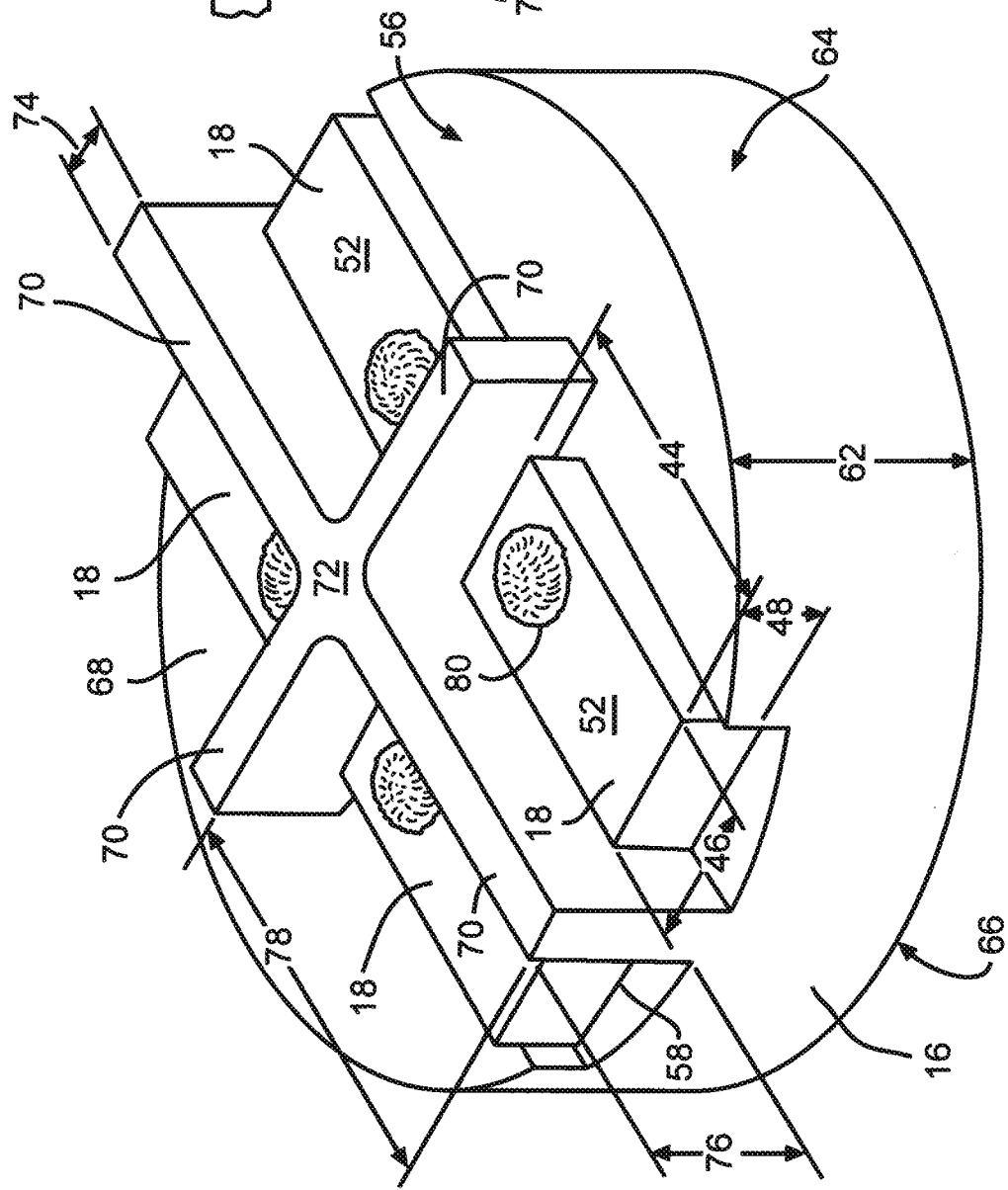

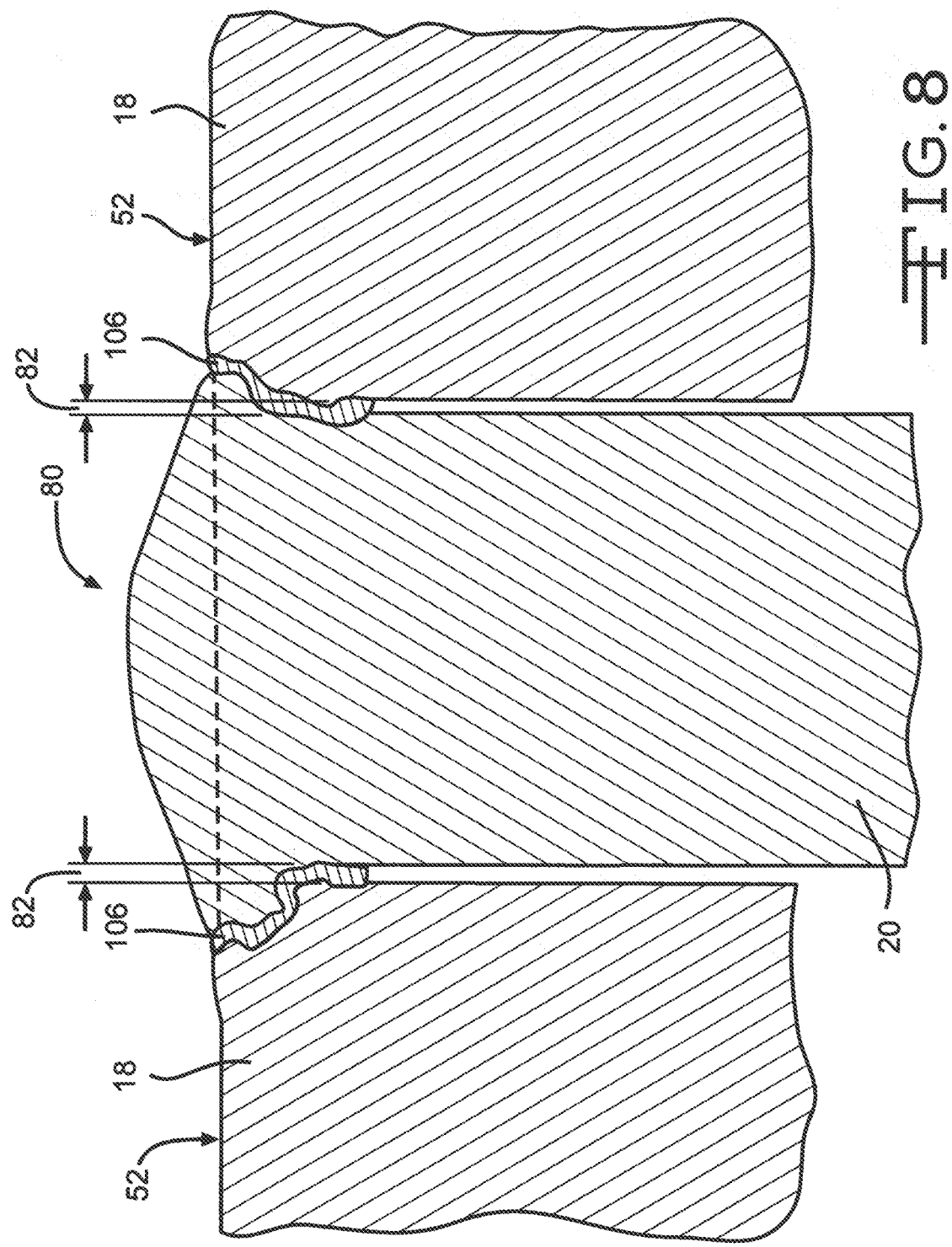

FULL PERIMETER LASER BEAM BUTTON WELD OF DISSIMILAR MATERIALS

CROSS-REFERENCE TO RELATED APPLICATIONS

This application claims priority from U.S. Provisional Patent Application Ser. No. 61/352,612 filed Jun. 8, 2010.

FIELD OF THE INVENTION

This invention relates generally to a hermetic feedthrough terminal pin assembly, preferably of the type incorporating a filter capacitor. More specifically, this invention relates to a method of welding two dissimilar metals into feedthrough filter capacitor assemblies, particularly of the type used in implantable medical devices such as cardiac pacemakers, cardioverter defibrillators, and the like, to decouple and shield internal electronic components of the medical device from undesirable electromagnetic interference (EMI) signals.

PRIOR ART

Feedthrough assemblies are generally well known in the art for use in connecting electrical signals through the housing or case of an electronic instrument. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical, device. The conductive terminals are fixed into place using a gold brazing process, which provides a hermetic seal between the pin and insulative material.

Since feedthrough assemblies such as these are implanted in human bodies, it is generally preferred that the materials used to construct such assemblies are biocompatible. These biocompatible materials, although commonly considered to be immune to the human body, generally have different material properties. These differing material properties such as melting temperature, thermal expansion, thermal conductivity and electrical conductivity make these materials diffult to join and construct into a feedthrough assembly.

Feedthrough assemblies generally comprise an insulative body, a supporting ferrule, and a plurality of electrically conductive feedthrough terminal pins that are hermetically sealed in the insulative body. In some cases, a capacitor is also incorporated into the assembly to provide protection from electromagnetic interference (EMI). With respect to the present invention, additional metallic terminal blocks, incorporated with a polymeric body, are integrated in the feedthrough assembly. Nevertheless, the electrically conductive feedthrough terminal pins are preferrably electrically connected to these metallic terminal blocks located adjacent the polymeric body.

Terminal pins have been composed of niobium and niobium alloys. Niobium and niobium alloys are biocompatible refractory metals that are cost effective. The niobium material provides good mechanical strength and electrical conduction, which adds to the durability and performance of the feedthrough. However the refractive nature of the niobium metal makes it a difficult material with which to join to other metals, particularly non-refractive metals such as nickel.

Traditional methods of joining dissimiliar metals such as a refractive metal to a non-refractive metal, typically result in cracking of the joint. This is particularly the case when niobium and nickel are joined together. Such joint cracks tend to create pathways for the introduction of undesirable debris and contamination. Debris and contamination could enter the assembly and potentially affect the electrical performance of the feedthrough assembly and/or connected device. What is desired is a feedthrough assembly and method of assembly thereof that produces a crack free joining of dissimiliar metals, for example of a refractive metal and a non-refractive metal, particularly the metals niobium and nickel.

In conjunction with the difficulties in joining dissimilar metals, other constraints from adjacent materials of the feedthrough assembly present additional difficulties that need to be overcome in constructing feedthrough assemblies. For example, the generally lower melting temperatures of adjacent polymeric bodies provide additional constraining parameters, particularly when they are located adjacent to where dissimilar metals are being joined together. The present invention addresses these problems as it relates to the construction of feedthrough assemblies. The present invention further provides an optimal construction and joining process thereof by which dissimilar metals are joined in the construction of feedthrough assemblies.

SUMMARY OF THE INVENTION

In a preferred form, a feedthrough filter capacitor assembly according to the present invention comprises an outer ferrule hermetically sealed to either an alumina insulator or fused glass dielectric material seated within the ferrule. The insulative material is also hermetically sealed to at least one terminal pin. That way, the feedthrough assembly prevents leakage of fluid, such as body fluid in a human implant application, past the hermetic seal at the insulator/ferrule and insulator/terminal pin interfaces.

According to the invention, the terminal pin of a feedthrough assembly, and preferably of the feedthrough filter capacitor assembly, is composed of a biocompatible refractive metal, such as niobium. The terminal pin can be a uniform wire-type structure of niobium or an alloy thereof. In that respect, niobium is a corrosion resistant material that provides a more cost effective terminal pin than other conventional metals, such as platinum or platinum-iridium terminal pins. Furthermore, terminal pins composed of niobium achieve the same benefits of biocompatibility, good mechanical strength, electrical conduction and a reliable hermetic feedthrough seal.

A plurality of terminal blocks are each preferably positioned in a slot atop a polymeric protective cap which preferably resides within the proximal region of the feedthrough assembly. The plurality of terminal blocks, preferably composed of an electrically conductive metal such as nickel, provide a preferred means of electrically attaching the feedthrough assembly to a medical device.

These terminal blocks provide a larger surface area with which to attach electrical connections between the feedthrough assembly and the medical device. The protective cap, preferably composed of a biocompatible polymeric material, electrically insulates each individual terminal block and protects the feedthrough assembly from possible mechanical damage.

The specific design parameters and material properties comprising the feedthrough assembly of the present invention present particular constraints regarding connection of the terminal pin to the terminal block. As such, the present invention relates to a feedthrough assembly and manufacturing process thereof that provides a robust crack free full perimeter joint about the terminal pin to effectively join the dissimilar metals of the terminal pin and terminal block. In addition, joining the terminal pin to the terminal block, without causing damage to the adjacent polymeric protective cap, is discussed.

These and other objects and advantages of the present invention will become increasingly more apparent by a reading of the following description in conjunction with the appended drawings.

BRIEF DESCRIPTION OF THE DRAWINGS

FIG. 1 is a perspective view of a feedthrough filter capacitor assembly.

FIG. 2 is top view of the feedthrough filter capacitor assembly shown in FIG. 1.

FIG. 4 is a magnified perspective view of the filter capacitor assembly shown in FIG. 1.

FIG. 5 is a magnified top view showing an embodiment of one of the welds of the present invention.

FIG. 8 illustrates a cross-section of a preferred weld embodiment of the present invention.

DETAILED DESCRIPTION OF THE PREFERRED EMBODIMENTS

Figure 3:
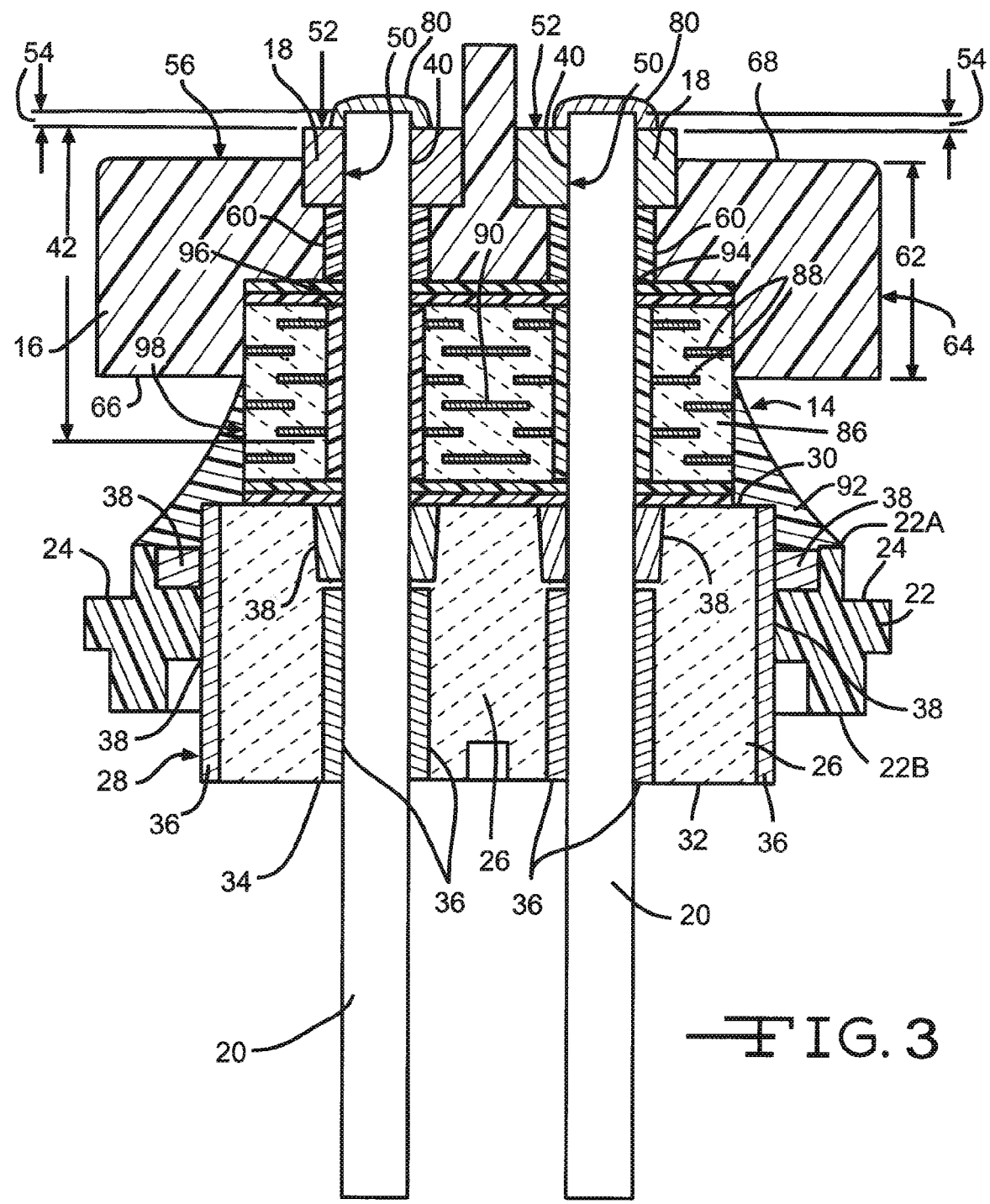
FIG. 3 is cross sectional view of the filter capacitor assembly shown in FIG. 1.
Figure 9:
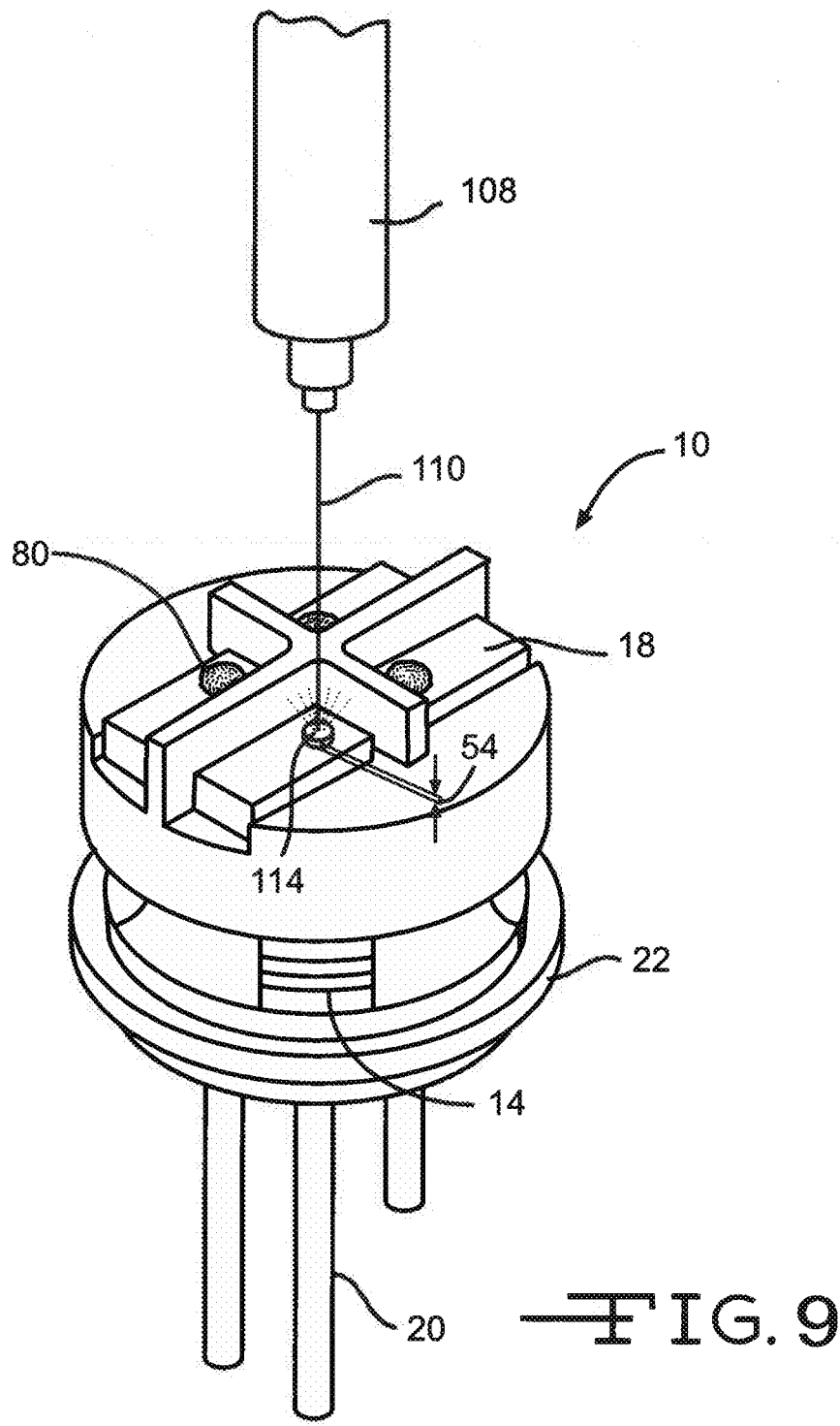
FIG. 9 illustrates a preferred embodiment of an assembly process of the present invention.

Referring now to the drawings, FIGS. 1, 3, and 9 show an internally grounded feedthrough capacitor assembly 10 comprising a feedthrough 12 supporting a discoidal filter capacitor 14, a protective cap 16, and a plurality of terminal blocks 18.

The feedthrough filter assembly 10 is useful with medical devices, preferably implantable devices such as pacemakers, cardiac defibrillators, cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like. The feedthrough 12 portion of the assembly 10 includes terminal pins 20 that provide for coupling, transmitting and receiving electrical signals to and from a patient's heart, while hermetically sealing the interior of the medical instrument against ingress of patient body fluids that could otherwise disrupt instrument operation or cause instrument malfunction. While not necessary for accomplishing these functions, it is desirable to attach the filter capacitor 14 to the feedthrough 12 for suppressing or decoupling undesirable EMI signals and noise transmission into the interior of the medical device.

More particularly, the feedthrough 12 of the feedthrough filter capacitor assembly 10 comprises a ferrule 22 defining an insulator-receiving bore formed by a ferrule sidewall extending from a first ferrule end 22A to a second ferrule end 22B, the ferrule sidewall surrounding an insulator 26. Suitable electrically conductive materials for the ferrule 22 include titanium, tantalum, niobium, stainless steel or combinations of alloys thereof, the former being preferred. The ferrule 22 may be of any geometry, non-limiting examples being round, rectangle, and oblong. A surrounding flange 24 (FIG. 3) extends from the ferrule 22 to facilitate attachment of the feedthrough 12 to the casing (not shown) of, for example, one of the previously described implantable medical devices. The method of attachment may be by laser welding or other suitable methods.

The insulator 26 is of a ceramic material such as of alumina, zirconia, zirconia toughened alumina, aluminum nitride, boron nitride, silicon carbide, glass or combinations thereof. Preferably, the insulating material is alumina, which is highly purified aluminum oxide, and comprises a sidewall 28 extending to a first upper side or end 30 and a second lower side or end 32. The insulator 26 is also provided with bores 34 that receive the terminal pins 20 passing therethrough. A layer of metal 36, referred to as metallization, is applied to the insulator sidewall 28 and to the sidewall of the terminal pin bores 34 to aid a braze material 38 in hermetically sealing between the ferrule 22 and the outer sidewall 28 of the insulator 26 and between the terminal pins 20 and the bores 34 of the insulator 26, respectively.

Suitable metallization materials 36 include titanium, titanium nitride, titanium carbide, iridium, iridium oxide, niobium, tantalum, tantalum oxide, ruthenium, ruthenium oxide, zirconium, gold, palladium, molybdenum, silver, platinum, copper, carbon, carbon nitride, and combinations thereof. The metallization layer may be applied by various means including, but not limited to, sputtering, electron-beam deposition, pulsed laser deposition, plating, electroless plating, chemical vapor deposition, vacuum evaporation, thick film application methods, and aerosol spray deposition, and thin cladding.

Non-limiting examples of braze materials 38 include gold, gold alloys, and silver. Then, if the feedthrough 12 is used where it will contact bodily fluids, the resulting brazes do not need to be covered with a biocompatible coating material. In other embodiments, if the brazes are not biocompatible, for example, if they contain copper, they are coated with a layer/ coating of biocompatible/biostable material. Broadly, the biocompatibility requirement is met if contact of the braze/ coating with body tissue and blood results in little or no immune response from the body, especially thrombogenicity (clotting) and encapsulation of the electrode with fibrotic tissue. The biostability requirement means that the braze/ coating remains physically, electrically, and chemical constant and unchanged over the life of the patient.

According to one embodiment of the invention, the terminal pins 20 are preferably composed of a first metal comprising a refractory metal. A refractory metal is herein defined as a metal that is resistant to heating and has a melting temperature greater than about 1,800° C. Non-limiting examples of refractory metals include niobium, molybdenum, tantalum, tungsten, rhenium, titanium, vanadium, zirconium, hafnium, osmium, iridium, and alloys thereof. In a more preferred embodiment, the terminal pins 20 comprise niobium and niobium alloys.

As shown in FIGS. 1-5, 8, 8A, and 9, each terminal pin 20 is received in a throughbore 40 of the terminal block 18. In a preferred embodiment, a proximal end portion 42 of the terminal pin 20 is received in the throughbore 40 of the terminal block 18. Terminal blocks 18 have a terminal block length 44, a terminal block width 46 and a terminal block height 48 (FIG. 4). In a preferred embodiment, the length 44 of the terminal block 18 ranges from about 1 mm to about 5 mm, the width 46 of the terminal block 18 ranges from about 1 mm to about 5 mm and the height 48 of the terminal block 18 ranges from about 0.05 mm to about 5 mm.

It is preferred that the terminal block 18 is composed of a second metal comprising an electrically conductive metal.

Non-limiting examples of conductor block 18 second metals include nickel, titanium, gold, silver, platinum, palladium, stainless steel, MP35N, and alloys thereof. In a more preferred embodiment, terminal blocks 18 are composed of nickel or a nickel alloy.

Each throughbore 40 of the terminal block 18 is preferably constructed with a diameter ranging from about 0.01 mm to about 0.10 mm such that the terminal pin 20 can pass therethrough. It is preferred that the terminal pin 20 is positioned such that the bore wall 50 of the terminal block 18 circumferentially surrounds the diameter of the terminal pin 20. It is further preferred that an end portion 54 of the terminal pin 20 resides above the topside surface 52 of the terminal block 18 (FIGS. 3 and 9). In a preferred embodiment, the terminal pin 20 resides from about 0.02 mm to about 0.2 mm above the top surface 52 of the terminal block 18. Although it is preferred that the end portion 54 of the terminal pin 20 is positioned above the topside surface 52 of the terminal block 18, it is contemplated that the end portion 54 of the terminal pin 20 may be positioned below the top surface 52 of the terminal block 18.

Furthermore, each terminal block 18 is preferably positioned on the topside 56 of a protective cap 16. In a preferred embodiment, the terminal block 18 resides within a slot 58 formed into the topside surface 56 of the protective cap 16 (FIGS. 1, 4). Each slot 58 is dimensioned such that the width 46 and length 44 of the terminal block 18 fit within the slot 58.

In addition, the terminal pins 20 are preferably positioned such that they are received through a throughbore 60 of the protective cap 16. More specifically, the proximal portion 42 of the terminal pin 20 is received through the respective throughbores 60 and 40 of the protective cap 16 and the terminal block 18. The protective cap 16 is positioned in a more distal location of the terminal pin 20 than the terminal block 18 (FIG. 3).

In a preferred embodiment, the protective cap 16 is composed of a biocompatible polymeric material that can withstand temperatures up to about 300° C. It is preferred that the protective cap 16 is composed of a polyoxymethylene copolymer such as CELCON® M450 or HOSTAFORM® C 52021 manufactured by Ticona of Florence, Ky. Other non-limiting materials comprising the protective cap 16 include silicone rubber, acrylonitrile butadiene styrene (ABS), polyether ether ketone (PEEK), low and high density polyethylene, polyethylene chloride, polypropylene, acetal, acetylcellulose, acrylic resin, and polytetrafluoroethylene. In an alternate preferred embodiment, the protective cap 16 may also be composed of a ceramic insulator material.

In a preferred embodiment, as shown in FIGS. 1, 3, 4, and 9 the protective cap 16 has a height 62 defined by a protective cap sidewall 64 extending from a first protective cap end 66 to a second protective cap end 68, wherein the terminal pin 20 extends through a protective cap throughbore 60 extending from the first protective cap end 66 to the second protective cap end 68. As shown in FIG. 3, the terminal block 18 is positioned in a stacked relationship on the topside surface 56 of the protective cap 16. The respective throughbores 60, 40 of the protective cap 16 and terminal block 18 are aligned such that the proximal region 42 of the terminal pin 20 resides therethrough. It should be noted however, that the protective cap 16 may or may not be incorporated with a feedthrough assembly 10 comprising a capacitor 14.

In addition, the protective cap 16 is constructed such that a plurality of walls 70 project from the topside surface 56 of the protective cap 16. More preferably, these walls 70 interconnect at a central junction 72 (FIG. 4). These walls 70 have a preferred wall thickness 74 of about 0.5 mm to about 5 mm, a preferred wall height 76 of about 1 mm to about 10 mm, and a preferred wall length 78 of about 1 mm to about 10 mm. The walls 70 electrically insulate the terminal blocks 18 from each other.

In a specific embodiment of joining niobium to that of nickel, it is preferred that a weld 80 of increased niobium content is formed. Such a weld 80 of increased niobium content is preferred because it reduces mechanical stresses within the niobium-nickel weld 80, thereby increasing the robustness and minimizing weld cracking.

Figure 6:
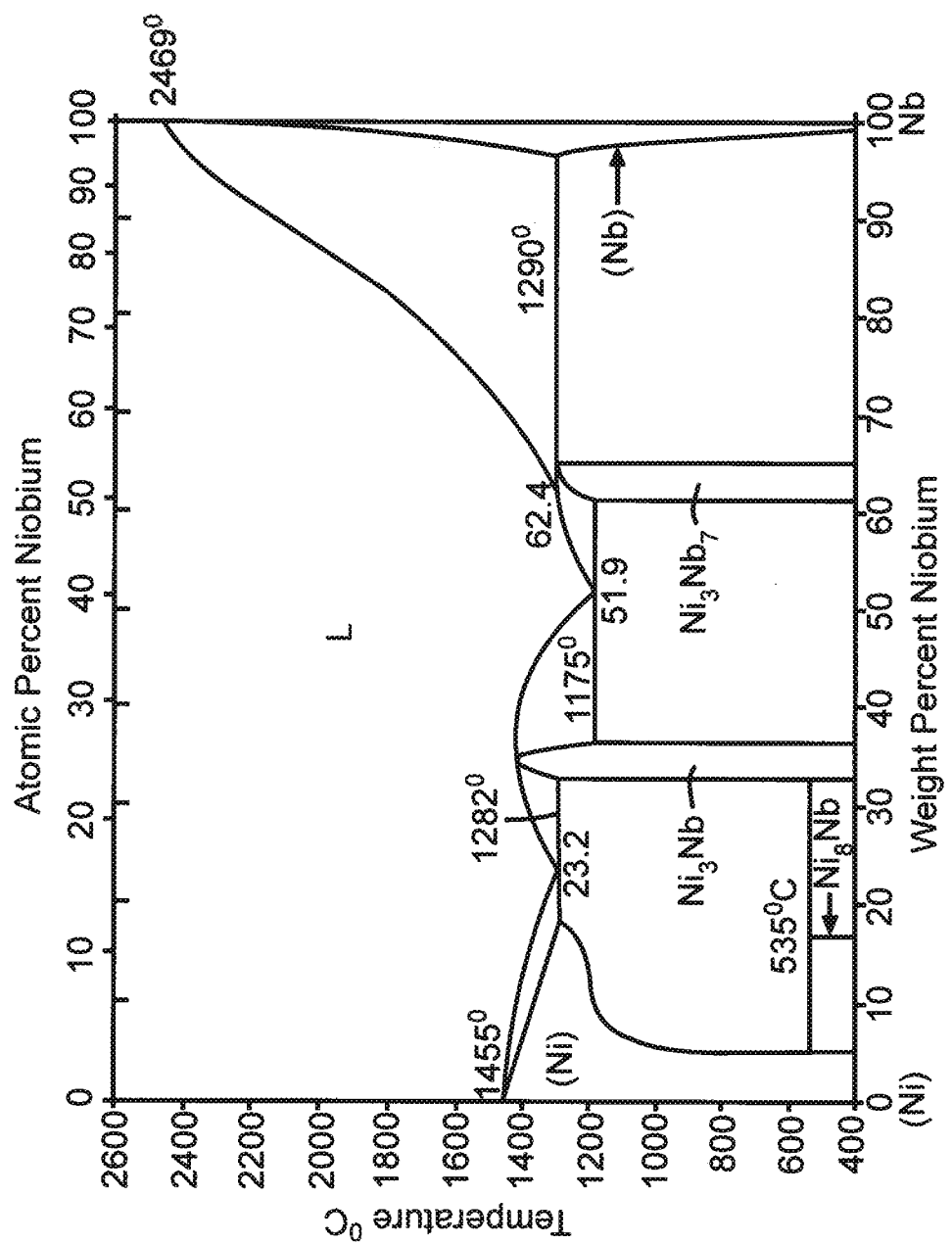
FIG. 6 is an illustration of a nickel-niobium binary phase diagram.

It is believed that the increased robustness of the weld 80 of the present invention is attributed to the increased niobium content. As can be seen in the nickel-niobium binary phase diagram, illustrated in FIG. 6, an increased niobium content with respect to nickel, reduces the occurrence of inter-metallic phases. As illustrated in the diagram of FIG. 6, there are fewer inter-metallic phases, such as $Ni_3Nb_7$ and $Ni_3Nb$, above about 65 weight percent niobium.

Figure 8A:
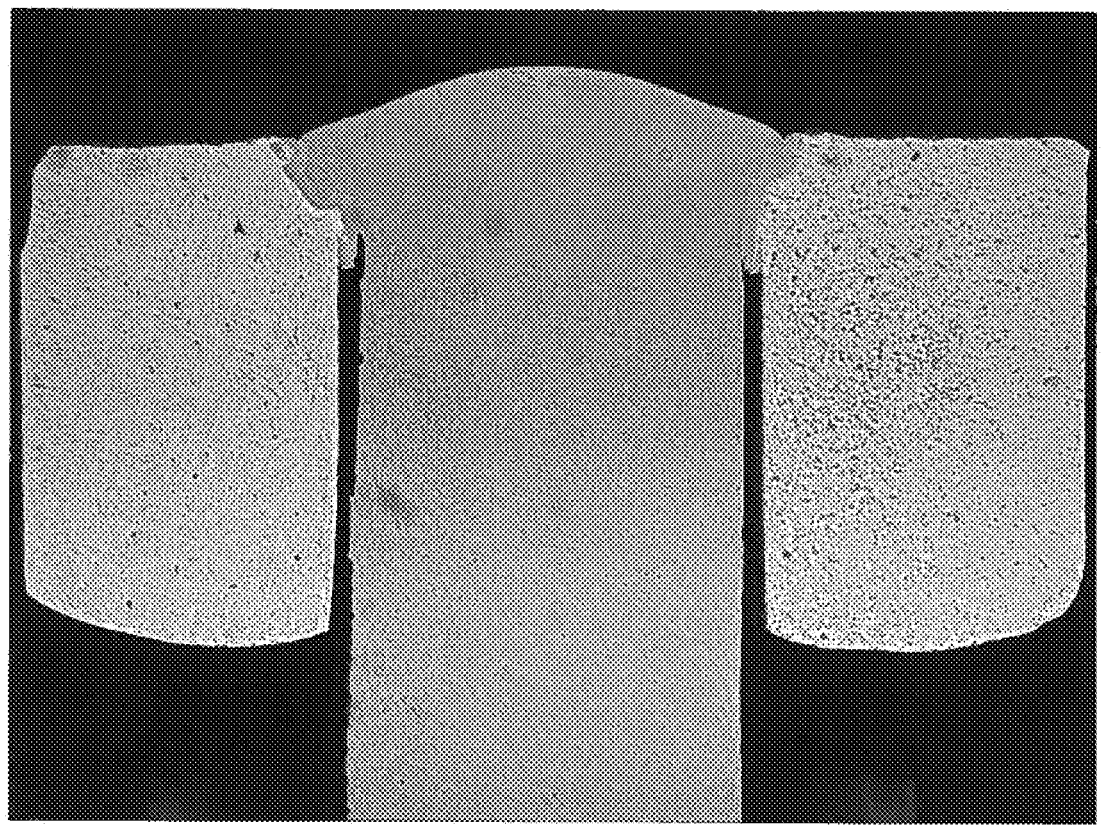
FIG. 8A shows a cross-sectional micrograph image of a preferred weld embodiment of the present invention.

In a preferred embodiment, a full perimeter weld 80 is formed between the first metal of the terminal pin 20 and the second metal of the terminal block 18. More specifically, the weld 80 is formed between the first metal of the terminal pin 20 and terminal block 18, such that weld encompasses the full perimeter 84 of the terminal pin 20. This is shown in FIGS. 1, 2, 4 and 5. It is preferred that the weld 80 is formed about the proximal end region 54 of the terminal pin 20. It is also preferred that the weld 80, as shown in FIGS. 1-5, 8, 8A, and 9, is formed of a shape similar to that of a "button". As illustrated in the cross-sectional view of FIG. 3, this "button" shaped weld 80 is formed above the top surface 52 of the terminal block 18. A "button weld" is herein defined as a weld having the general shape and appearance of that of a button as illustrated in FIGS. 8 and 8A.

In a preferred embodiment, an alloy is formed comprising a mixture of the first metal of the terminal pin 20 and the second metal of the terminal block 18. In a preferred embodiment, an alloy comprising about 65 weight percent to about 95 weight percent of the first metal is combined with about 35 weight percent to about 5 weight percent of the second metal. In a more preferred embodiment, a weld 80 comprising from about 65 to about 95 weight percent niobium as the first metal is combined with about 35 to about 5 weight percent nickel as the second metal of the terminal block.

Figure 7:
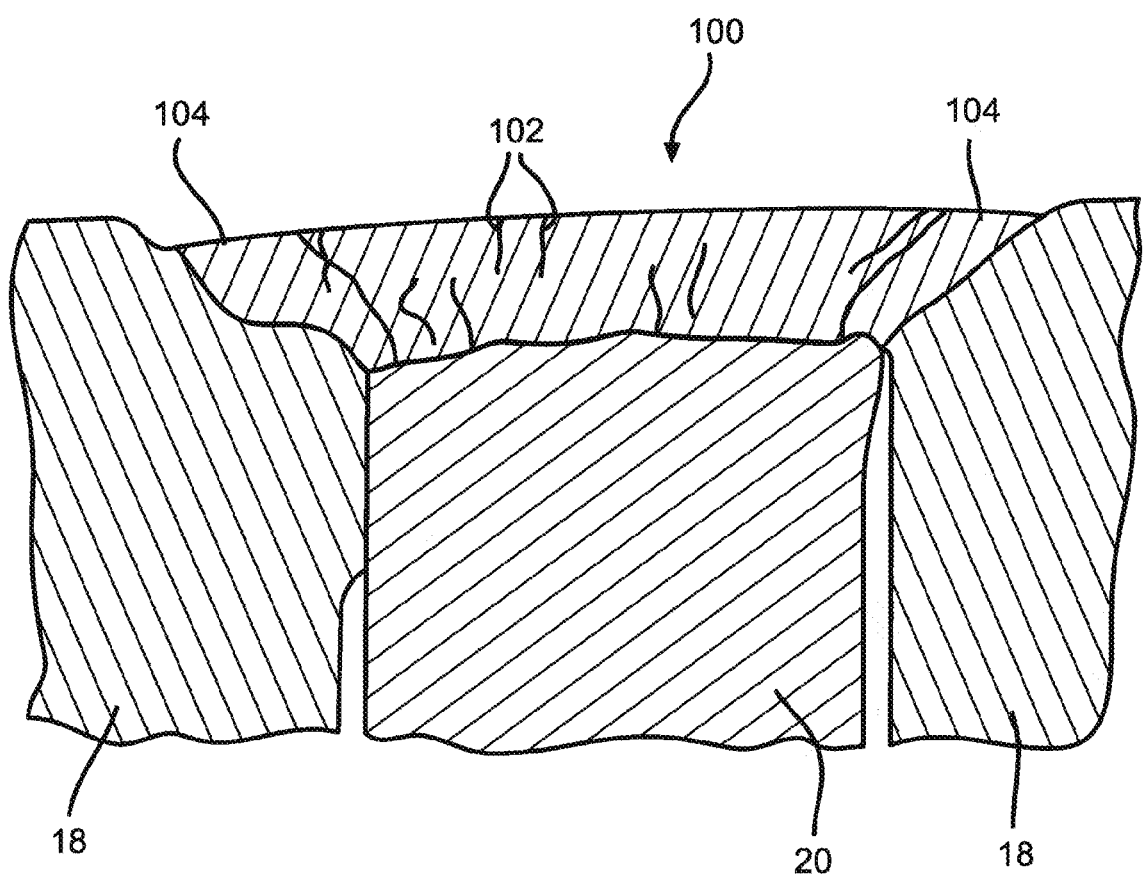
FIG. 7 shows a cross-sectional illustration of a prior art weld.
Figure 7A:
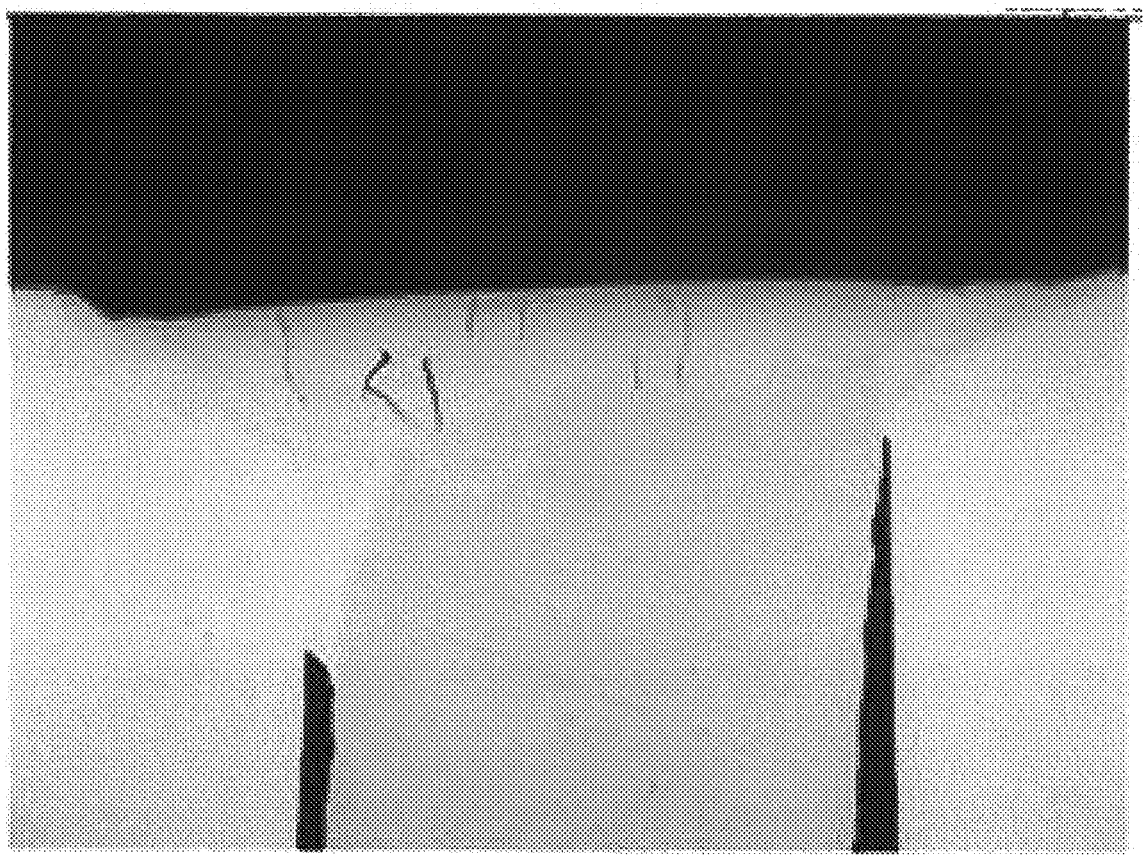
FIG. 7A shows a cross-sectional micrograph image of a prior art weld.

As previously mentioned, a niobium content of greater than about 65 weight percent provides for a niobium-nickel alloy with few inter-metallic phases. A weld 100 (FIGS. 7, 7A) comprising inter-metallic phases typically results in an undesirably brittle weld that is prone to cracking. FIGS. 7 and 7A illustrate a cross-sectional view of a prior art weld 100 having cracks 102 therewithin. Weld cracks 102, such as those illustrated and shown in FIGS. 7 and 7A, are typically formed during prior art joining processes. It is possible that a crack 102 or multiple cracks 102 could propagate through the weld 100, creating a pathway for the entry of undesirable debris that could disrupt the performance of the feedthrough assembly 10 and/or medical device. In contrast, the weld $0 of the present invention lacks these cracks 102 of the prior art weld 100, as shown in the cross-sectional views of FIGS. 8 and 8A.

As shown in the illustration and micrograph of FIGS. 7 and 7A, respectively, prior art weld 100 has an appearance of a flat "nail head" which is unlike the preferred "button" shape of the present invention weld 80. It is believed that the curved shape of the preferred "button" weld 80 acts as a stress reducer that contributes to the increased robustness of the present weld 80.

Furthermore, as shown in the cross-sectional micrograph image of the present weld 80 of FIG. 8A, and the illustration of FIG. 8, there is a distinct boundary layer 106 positioned on either side of the weld 80. This boundary layer 106 delineates the first metal of the terminal pin 20 from the second metal of the terminal block 18. As shown in the illustration and micrograph of FIGS. 8 and 8A, the "button weld" 80 is distinguished from the prior art weld 100 shown in FIGS. 7 and 7A by the presence of the boundary layer 106, a well defined distinct region comprising a mixture of the first metal of the terminal pin 20 and the second metal of the terminal block 18. As shown, the boundary layer 106 has a well defined width 82 extending from the top surface 52 of the terminal block 18 to a position distally from the top surface 52.

Unlike the weld 80 of the present invention, the prior art weld 100 as shown in the micrograph of FIG. 7A, does not have a distinct boundary layer 106. The prior art weld 100 is characterized by a weld gradient region 104 in which the first metal of the terminal pin 20 appears to gradually diffuse or transition into the second metal of the terminal block 18. This weld gradient region 104 appears of a distinct shade of grey, contrasting between the darker and lighter shades of grey of the terminal pin 20 and terminal block 18, respectively.

It is believed that the combination of the curved "button" like weld shape and the distinct boundary layers 106 between the first and second metals contributes to the reduced mechanical stress, therefore enabling a crack free weld. In addition, it is believed that the weld gradient region 104 of the prior art weld 100, comprises undesirable inter-metallic phases that contribute to its brittleness.

The present button weld 80 is manufactured during a welding process by a beam 110 of laser energy focused at a center region 114 of the end 54 of the terminal pin 20, as illustrated in FIG. 9. Focusing the laser energy at substantially the center 114 of the terminal pin 20 provides a concentration of heat there that melts and deforms the first metal of the terminal pin 20. By focusing the heat energy at the center region 114 of the end 54 of the terminal pin 20, the first metal content of the weld 80 is increased. A sufficient amount of heat is generated to effectively form the alloy joining the two dissimilar first and second metals 20, 18 without generating too much heat such that the protective cap 16 and other adjacent materials of the feedthrough assembly 10 are damaged. In addition, focusing the beam of laser energy 110 about the center region 114 of the end 54 of the terminal pin 20, dissipates the energy away from the protective cap 16 thereby minimizing degradation of the adjacent cap 16.

In a preferred embodiment, a laser welding instrument 108 (FIG. 9) such as a Lasag® model SLS200 is used to join the terminal pin 20 to the terminal block 18. In a preferred embodiment, a laser pulse frequency of between about 10 Hz to about 30 Hz is used with a pulse width of between about 1.0 ms to about 5.0 ms to thereby generate a welding energy of from about 1.0 J to about 5.0 J to weld the dissimilar metals together. These preferred laser welding parameters provide a full perimeter weld 80 that sufficiently joins the two dissimilar metals of the terminal pin 20 and terminal block 18.

As further shown in FIGS. 2, 4 and 5, the feedthrough assembly 10 includes the filter capacitor 14 that provides for filtering undesirable EMI signals before they can enter the device housing via the terminal pins 20. The filter capacitor 14 comprises a ceramic or ceramic-based dielectric monolith 86 having multiple capacitor-forming conductive electrode plates formed therein. The capacitor dielectric 86 preferably has a circular cross-section matching the cross-section of the ferrule 22 and supports a plurality of spaced-apart layers of first or "active" electrode plates 88 in spaced relationship with a plurality of spaced apart layers of second or "ground" electrode plates 90. The filter capacitor 14 is preferably joined to the feedthrough 12 adjacent to the insulator side 30 by an annular bead 92 of conductive material, such as a solder or braze ring, or a thermal-setting conductive adhesive, and the like. The dielectric 86 includes lead bores 94 provided with an inner surface metallization layer. The terminal pins 20 pass there through and are conductively coupled to the active plates 88 by a conductive braze material 96 contacting between the terminal pins 20 and the bore metallization. In a similar manner, the ground plates 90 are electrically connected through an outer surface metallization 98 and the conductive material 92 to the ferrule 22.

It is appreciated that various modifications to the invention concepts described herein may be apparent to those of ordinary skill in the art without departing from the scope of the present invention as defined by the appended claims.

What is claimed is:

1. A feedthrough assembly, which comprises:
a) an insulator of electrically non-conductive material having a first height defined by an insulator sidewall having an outer insulator surface extending from a first insulator end to a second insulator end, wherein the insulator has at least one terminal pin bore extending there through to the first and second insulator ends;
b) a terminal pin comprising a first metal received in the terminal pin bore, the terminal pin having a terminal pin sidewall extending from a first terminal pin portion having a first terminal pin end to a second terminal, pin end, wherein the opposed first and second terminal pin ends are spaced from the respective first and second insulator ends;
c) a ferrule of an electrically conductive material comprising a ferrule opening defined by a surrounding ferrule sidewall having an inner ferrule surface, wherein the insulator is supported in the ferrule opening;
d) a terminal block of a second metal and comprising a terminal block sidewall extending to opposed first and second terminal block ends, the terminal block having at least one terminal block bore extending there through to the first and second terminal block ends, wherein the first terminal pin portion extends through the terminal block bore with the first terminal pin end spaced above the first end of the terminal block and the second end of the terminal block facing the insulator;
e) a first braze material extending from a first metallization contacting the terminal pin bore to the first metal of the terminal pin thereby hermetically sealing the terminal pin to the insulator;
f) a second braze material extending from a second metallization contacting the outer insulator surface to the inner ferrule surface to thereby hermetically seal the insulator to the ferrule; and
a weld connecting the first portion of the terminal pin to the first end of the terminal block.

2. The feedthrough assembly of claim 1 wherein the first metal of the terminal pin comprises a refractory metal.

3. The feedthrough assembly of claim 1 wherein the first metal of the terminal pin is selected from the group consisting of niobium, molybdenum, tantalum, tungsten, rhenium, titanium, vanadium, zirconium, hafnium, osmium, iridium, and alloys thereof.

4. The feedthrough assembly of claim 1 wherein the second metal of the terminal block is selected from the group consisting of nickel, titanium, gold, silver, platinum, palladium, stainless steel, MP35N, and alloys thereof.

5. The feedthrough assembly of claim 1 wherein the weld is a laser weld formed between a full perimeter of the terminal pin and the terminal block.

6. The feedthrough assembly of claim 5 wherein the laser weld is characterized as having been formed by a laser at a welding energy of from about 1.0 joule (J) to about 5.0 joules (J).

7. The feedthrough assembly of claim 5 wherein the laser weld is characterized as having been formed by a laser at a welding pulse frequency of from about 10 hertz (Hz) to about 30 hertz (Hz).

8. The feedthrough assembly of claim 5 wherein the laser weld is characterized as having been formed by a laser at a welding pulse width of from about 1.0 milliseconds (msec) to about 5.0 milliseconds (msec).

9. The feedthrough assembly of claim 5 wherein the laser weld is characterized as having been formed by a laser beam focused about a center region of the first end of the terminal pin.

10. The feedthrough assembly of claim 1 wherein the weld comprises from about 65 to about 95 weight percent of the first metal of the terminal pin and from about 5 to about 35 weight percent of the second metal of the terminal block.

11. The feedthrough assembly of claim 1 wherein the weld is characterized by a boundary layer that delineates the first and second metals of the respective terminal pin and terminal block.

12. The feedthrough assembly of claim 1 further comprising a protective cap having a second height defined by a protective cap sidewall extending from a first protective cap end to a second protective cap end, wherein the protective cap is positioned between the second end of the terminal block and the first end of the insulator with the terminal pin residing in a protective cap throughbore extending to the first and second protective cap ends.

13. The feedthrough assembly of claim 12 wherein the protective cap is composed of a biocompatible polymeric material.

14. The feedthrough assembly of claim 12 wherein the terminal block is positioned in a slot formed within a surface at the first end of the protective cap.

15. The feedthrough assembly of claim 1 wherein the first end of the terminal pin resides from about 0.02 millimeters to about 0.2 millimeters above a top surface of the terminal block at the first terminal block end.

16. A feedthrough assembly, which comprises:
a) an insulator of electrically non-conductive material having a first height defined by an insulator sidewall having an outer insulator surface extending from a first insulator end to a second insulator end, wherein the insulator has at least one terminal pin bore extending there through to the first and second insulator ends;
b) a terminal pin comprising a first metal received in the terminal pin bore, the terminal pin having a terminal pin sidewall extending from a first terminal pin portion having a first terminal pin end to an second terminal pin end, wherein the opposed first and second terminal pin ends are spaced from the respective first and second insulator ends;
c) a ferrule of an electrically conductive material comprising a ferrule opening defined by a surrounding ferrule sidewall having an inner ferrule surface, wherein the insulator is supported in the ferrule opening;
d) a terminal block of a second metal and comprising a terminal block sidewall extending to opposed first and second terminal block ends, the terminal block having at least one terminal block bore extending there through to the first and second terminal block ends, wherein the first terminal pin portion resides in the terminal block bore with the first terminal pin end recessed below the first end of the terminal block and the second end of the terminal block facing the insulator;
e) a first braze material extending from a first metallization contacting the terminal pin bore to the first metal of the terminal pin to thereby hermetically seal the terminal pin to the insulator;
f) a second braze material extending from a second metallization contacting the outer insulator surface to the inner ferrule surface to thereby hermetically seal the insulator to the ferrule; and
g) a weld connecting the first end of the terminal pin to the first end of the terminal block, wherein the weld is characterized as having been formed by a laser beam focused about a center region of the first end of the terminal pin.

17. The feedthrough assembly of claim 16 further comprising a protective cap having a second height defined by a protective cap sidewall extending from a first protective cap end to a second protective cap end, wherein the protective cap is positioned between the second end of the terminal block and the first end of the insulator with the terminal pin residing in a protective cap throughbore extending to the first and second protective cap ends, and wherein the terminal block is positioned in a slot formed within a surface at the first end of the protective cap.

18. A feedthrough assembly, which comprises:
a) an insulator of electrically non-conductive material having a first height defined by an insulator sidewall having an outer insulator surface extending from a first insulator end to a second insulator end, wherein the insulator has at least one terminal pin bore extending there through to the first and second insulator ends;
b) a terminal pin comprising niobium received in the terminal pin bore, the terminal pin having a terminal pin sidewall extending from a first terminal pin portion having a first terminal pin end to a second terminal pin end, wherein the opposed first and second terminal pin ends are spaced from the respective first and second insulator ends;
c) a ferrule of an electrically conductive material comprising a ferrule opening defined by a surrounding ferrule sidewall having an inner ferrule surface, wherein the insulator is supported in the ferrule opening;
d) a terminal block comprising nickel and having a terminal block sidewall extending to opposed first and second terminal block ends, the terminal block having at least one terminal block bore extending there through to the first and second terminal block ends, wherein the first terminal pin portion extends through the terminal block bore with the first terminal pin end spaced above the first end of the terminal block and the second end of the terminal block, facing the insulator;
e) a first braze material extending from a first metallization contacting the terminal pin bore to the terminal pin thereby hermetically sealing the niobium terminal pin to the insulator;
f) a second braze material extending from a second metallization contacting the outer insulator surface to the inner ferrule surface to thereby hermetically seal the insulator to the ferrule; and
g) a weld connecting the first portion of the niobium terminal pin to the first end of the nickel terminal block.

19. The feedthrough assembly of claim 18 wherein the weld is a laser weld characterized as having been formed by a laser at least one of a welding energy of from about 1.0 joule (J) to about 5.0 joules (J), a welding pulse frequency of from about 10 hertz (Hz) to about 30 hertz (Hz), and a welding pulse width of from about 1.0 milliseconds (msec) to about 5.0 milliseconds (msec).

20. The feedthrough assembly of claim 18 wherein the weld is characterized as having been formed by a laser beam focused about a center region of the first end of the terminal pin.

21. The feedthrough assembly of claim 18 wherein the weld comprises from about 65 to about 95 weight percent of the niobium of the terminal pin and from about 5 to about 35 weight percent of the nickel of the terminal block.

22. The feedthrough assembly of claim 18 wherein the weld is characterized by a boundary layer that delineates the niobium and nickel of the respective terminal pin and terminal block.

23. The feedthrough assembly of claim 18 further comprising a protective cap having a second height defined by a protective cap sidewall extending from a first protective cap end to a second protective cap end, wherein the protective cap is positioned between the second end of the terminal block and the first end of the insulator with the terminal pin residing in a protective cap throughbore extending to the first and second protective cap ends.

24. The feedthrough assembly of claim 23 wherein the protective cap is composed of a biocompatible polymeric material.

25. The feedthrough assembly of claim 23 wherein the terminal block is positioned in a slot formed within a surface at the first end of the protective cap.

26. The feedthrough assembly of claim 18 wherein the first end of the terminal, pin resides from about 0.02 millimeters to about 0.2 millimeters above a top surface of the terminal block at the first terminal block end.

\* \* \* \* \*

UNITED STATES PATENT AND TRADEMARK OFFICE
CERTIFICATE OF CORRECTION

PATENT NO. : 8,648,265 B2  Page 1 of 1
APPLICATION NO. : 13/155497
DATED : February 11, 2014
INVENTOR(S) : Ken Talamine et al.

It is certified that error appears in the above-identified patent and that said Letters Patent is hereby corrected as shown below:

In the claims

Column 8, line 30 (Claim 1, line 11) after the word "terminal" delete the ","

Column 8, line 55 (Claim 1, line 36) before the words "a weld" insert --g)--

Column 10, line 54 (Claim 18, line 27) after the word "block" delete the ","

Signed and Sealed this
Tenth Day of March, 2015

Michelle K. Lee
*Deputy Director of the United States Patent and Trademark Office*